United States Patent [19]

Adair

[11] Patent Number: 5,197,457

[45] Date of Patent: Mar. 30, 1993

[54] DEFORMABLE AND REMOVABLE SHEATH FOR OPTICAL CATHETER

[76] Inventor: Edwin L. Adair, 99 Inverness Dr. East, Englewood, Colo. 80112

[21] Appl. No.: 831,071

[22] Filed: Feb. 4, 1992

Related U.S. Application Data

[63] Continuation of Ser. No. 581,591, Sep. 12, 1990, abandoned.

[51] Int. Cl.$^5$ .................. A61B 1/06; A61M 5/178; A61M 25/00
[52] U.S. Cl. .................................. 128/7; 604/170; 604/282
[58] Field of Search .............. 604/51, 54, 55, 158, 604/164, 165, 170, 282; 128/4–11, 656–658, 772, 4 A, 4 SM

[56] References Cited

U.S. PATENT DOCUMENTS

| | | | |
|---|---|---|---|
| 3,605,725 | 9/1971 | Benton | 128/7 X |
| 3,854,473 | 12/1974 | Matsuo | 128/8 |
| 4,423,727 | 1/1984 | Widran et al. | 128/7 X |
| 4,589,404 | 5/1986 | Barath et al. | 128/7 X |
| 4,630,598 | 12/1986 | Bonnet | 128/7 |
| 4,717,380 | 1/1988 | Baumgartner | 128/7 X |
| 4,798,193 | 1/1989 | Giesy et al. | 128/7 |
| 4,799,474 | 1/1989 | Ueda | 128/4 SM |
| 4,882,777 | 11/1989 | Narula | 604/281 |
| 4,899,733 | 2/1990 | DeCastro et al. | 128/7 |
| 5,095,888 | 3/1992 | Hawley | 128/10 |

Primary Examiner—John D. Yasko
Assistant Examiner—Adam Cermak
Attorney, Agent, or Firm—Fields, Lewis, Pittenger & Rost

[57] ABSTRACT

A deformable sheath for an optical catheter is provided which includes an elongated, deformable hollow body having a normal predetermined shape which is compatible with its intended use in situ in a passageway in the patient. The body has a distal end and a proximate end with a plurality of channels extending therebetween. An optical catheter extends through one of the channels in the body, having a distal end aligned with the distal end of the body and a proximate end extending outwardly beyond the proximate end of the body, the catheter assuming the normal shape of the body. A substantially rigid guide wire is provided which is extendable through a second of the channels to straighten the body during insertion of the sheath into a passageway within the patient. This guide wire is removable from the body after insertion so that the body resumes its normal predetermined shape. The sheath can include a third channel for insertion of a laser fiber of laser lithotripsy or an electrohydraulic probe to fracture stones. A lock coupler is attached to the proximate end of the body for attachment to a fitting to properly align and connect the sheath and its catheter and other instruments with external instrumentation.

7 Claims, 1 Drawing Sheet

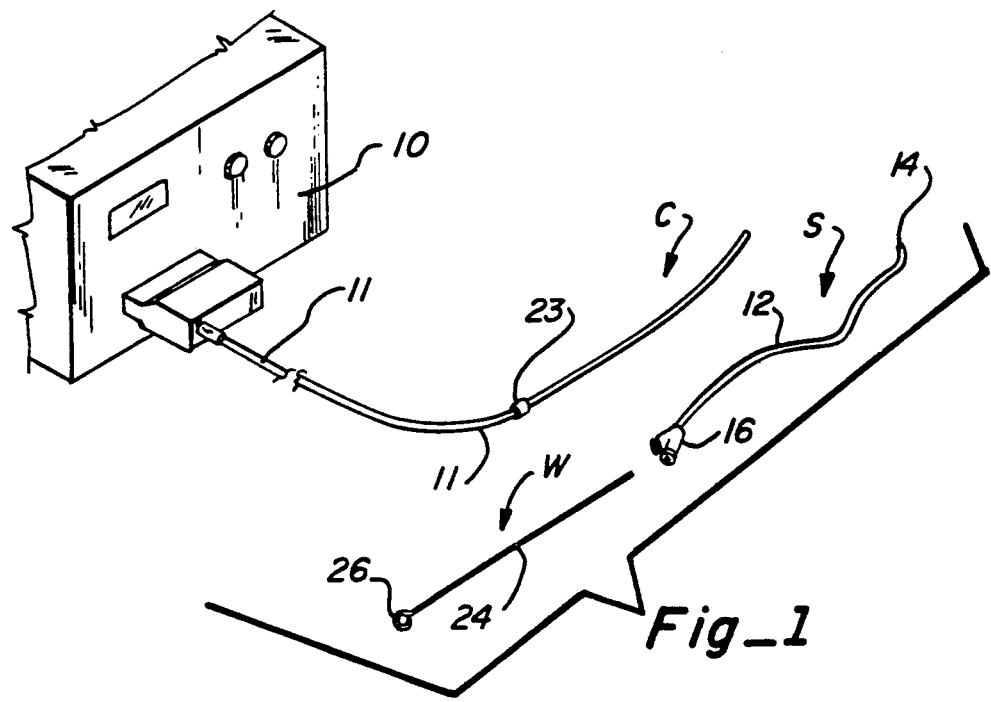
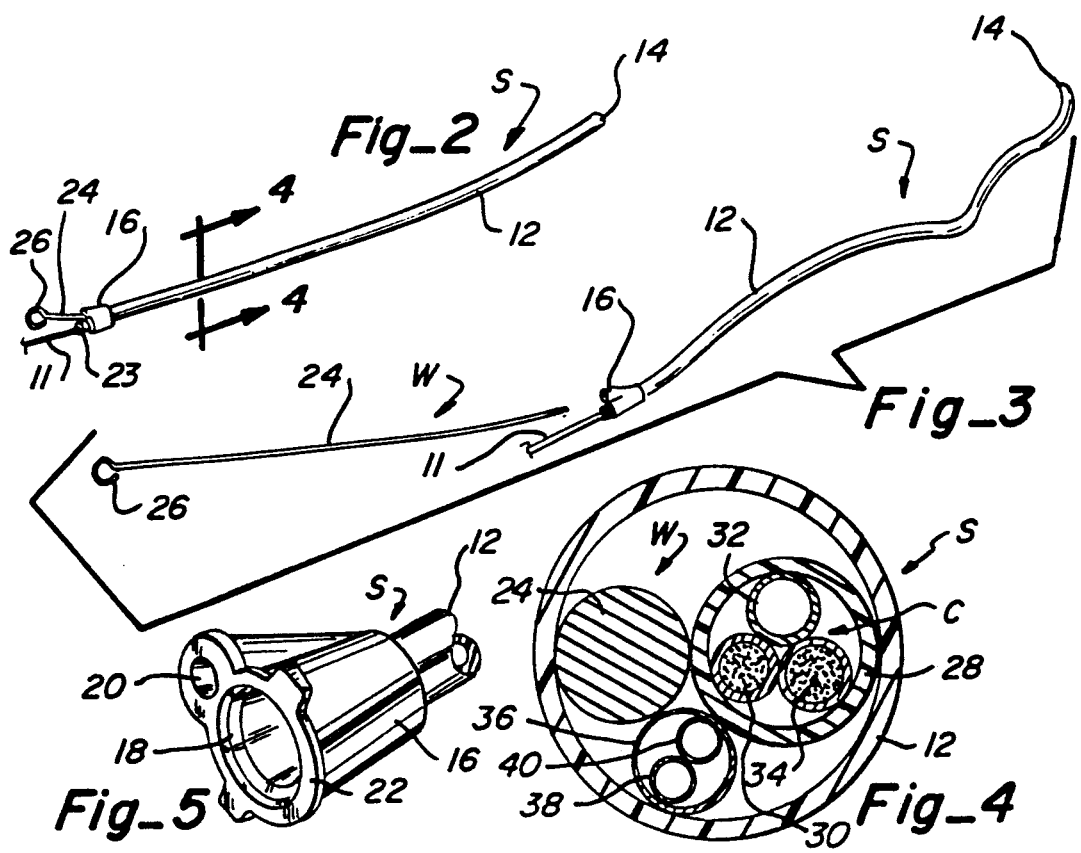

DEFORMABLE AND REMOVABLE SHEATH FOR OPTICAL CATHETER

This is a continuation of U.S. application Ser. No. 07/581,591 filed Sep. 12, 1990, now abandoned.

TECHNICAL FIELD

The present invention relates to a deformable and removable sheath and more particularly to a deformable and removable sheath for use with an optical catheter which can be straightened by a guide wire for insertion in the passageway leading to a body cavity of a patient and can be returned to its original shape after insertion by removal of the guide wire.

BACKGROUND ART

Most optical catheters on the market today are made in a conventional manner wherein they include an elongated body or shaft containing both image fibers and light carrying fibers. The catheter may also have additional passageways for irrigation and/or for conducting operative or investigative procedures. Sometimes it also will be provided with a steering mechanism for pointing the distal end thereof. Most optical catheters are configured in a shape to do one specific examination. For example, one may be a flexible cysto-urethroscope for examination of the lower genitourinary tract. Another may be a bronchoscope for looking into the respiratory tract. Still another may be a flexible hysteroscope for looking into the uterus. Once any of these devices is manufactured, it is locked into that configuration and generally can only be used for the purpose for which it was constructed. In other words, it is not adaptable for other types of examinations. An exception to this is that in rare instances one may use a flexible hysteroscope for looking into the bladder. If this is done only because the regular scope is broken or unavailable, or done by mistake. There also is a device now available for looking into the nasal sinuses. This is a small flexible scope which has an eyepiece, a steering mechanism for changing direction of the device to allow its manipulation into a sinus opening and a light connector. However, it cannot be used for any other purpose.

Because of the necessity for providing a variety of types and styles of catheters, the cost invested in optical catheters can be quite high, inasmuch as they are not interchangeable.

DISCLOSURE OF THE INVENTION

A deformable sheath for an optical catheter is provided which includes an elongated, deformable hollow body having a normal predetermined shape which is compatible with its intended use in situ in a passageway in the patient. The body has a distal end and a proximate end with a plurality of channels extending therebetween. An optical catheter extends through one of the channels in the body, having a distal end aligned with the distal end of the body and a proximate end extending outwardly beyond the proximate end of the body, the catheter assuming the normal shape of the body. A substantially rigid guide wire is provided which is extendable through a second of the channels to straightened the body during insertion of the sheath into a passageway within the patient. This guide wire is removable from the body after insertion so that the body resumes its normal predetermined shape. The sheath can include a third channel for insertion of a laser fiber or laser lithotripsy or an electrohydraulic probe to fracture stones. A lock coupler is attached to the proximate end of the body for attachment to a fitting to properly align and connect the sheath and its catheter to external instrumentation.

The guide wire can comprise a long slender body having a distal end and a proximate end receivable in the sheath body. A handle is attached to the proximate end of the guide wire body to aid in inserting and withdrawing the guide wire from the sheath.

With this invention, it can be seen that deformable sheaths of the type just described can be provided each having a different natural shape depending on its intended use. The catheter, which is quite expensive, can be removed from one sheath after use for one purpose and inserted in another sheath for use for another purpose. The sheath, which is inexpensive, can be disposable to minimize the transfer of disease or infection from one patient to the next.

Additional advantages of this invention will become apparent from the description which follows, taken in conjunction with the accompanying drawings.

BRIEF DESCRIPTION OF THE DRAWINGS

FIG. 1 is a perspective view showing a deformable and removable sheath and guide wire constructed in accordance with this invention for use with an optical catheter attached to a console;

FIG. 2 is a perspective view of the deformable and removable sheath of FIG. 1 with the guide wire in place;

FIG. 3 is a perspective view of the deformable and removable sheath with the guide wire removed;

FIG. 4 is an enlarged vertical section, taken along line 4—4 of FIG. 2, showing the interior of the guide wire with the sheath and catheter in place; and FIG. 5 is an enlarged perspective view of the proximate end of the deformable and removable sheath.

BEST MODE FOR CARRYING OUT THE INVENTION

In accordance with this invention, a sheath S is provided which may have a preformed curved shape as shown in FIG. 1 which is compatible with the shape of the passageway of a patient in which it is to be used. This sheath S can be slid over catheter C which is removably connected to a console 10, such as the type shown in U.S. Pat. No. 4,589,404. Since the catheter is flexible, it will assume the shape of sheath S when inserted therein. However, for insertion of the catheter and sheath into the passageway of the patient, a guide wire W is provided. Conveniently, the sheath S has a body 12 which forms one channel and has an open distal end 14 and a connector 16 at the proximate end. As best seen in FIG. 5, connector 16 has a central opening 18 for receiving the catheter C and a side opening 20 for receiving guide wire W. The central opening 18 is formed in a lock coupler in the form of a female luer lock 22 to allow attachment to a fitting which has a male luer adaptor so that the catheter will be positioned in a fixed position within the sleeve. The side opening 20 can receive the body 24 of guide wire W which is inserted and withdrawn by means of handle 26 on the proximate end thereof. Once inserted the guide wire W will straighten out the sheath to the position shown in FIG. 2 for easy insertion into a passageway in a patient's body.

As best seen in FIG. 4, catheter C is received in another channel 28 within sheath body or one channel 12. Conveniently, channel 28 can also receive devices, such as a laser fiber 30 for lithotripsy. Similarly, an irrigation passageway 32 can be provided. A fiber optic bundle 34 is also provided which may include one or more optic fibers for transmitting light from console 10 to the distal end of the catheter C to illuminate the site under investigation. In addition, bundle 34 will contain coherent fibers to project an image to a video screen (not shown) associated with console 10. When inserted, these elements will extend through channel 28 to the distal end 14 of sheath S. Once the sheath with the catheter and guide wire have been inserted into the passageway of the patient so that the distal end 14 of the sheath is properly positioned within a body cavity for observation and/or treatment, guide wire W is withdrawn and the sheath returns to its normal position, as shown in FIGS. 1 and 3 which conforms to the particular passageway for which it was designed. Of course, if observation and/or treatment is desired in a different bodily passageway, then a different sheath will be used with the same catheter and guide wire in the manner just described. The sheath can include an additional channel 36 for insertion of a laser fiber 38 or laser lithotripsy 40.

It will be understood from the foregoing, that preformed sleeves can be provided which are made of any shape, any diameter and almost any length. The shape given to the sleeve is dependant upon its use. For example, one curve is imparted to the body of the sheath for viewing the inside upper pole calys of the kidney. Still another shape is given to a sleeve for use with a catheter for viewing the inside of the middle calys. Still a third shape is used for viewing the inside lower calys of the kidney.

This invention has been described in detail with reference to a particular embodiment thereof, but it will be understood that various other modifications can be effected within the spirit and scope of this invention.

I claim:

1. Apparatus having a deformable and removable sheath, for use with an optical catheter wherein said sheath with a catheter therein is to be positioned in a passageway leading to a body cavity of a patient for observation and/or treatment, said apparatus comprising:
    an elongated, deformable, hollow body forming said sheath and having a normal predetermined shape which is compatible with its intended use in situ, said body having a distal end, a proximate end and a plurality of channels extending from said proximate end to said distal end;
    an optical catheter extendable through a first of said channels in said body, having a distal end aligned with said distal end of said body and a proximate end extending outwardly beyond said proximate end of said body, said catheter assuming the normal shape of said body;
    a substantially rigid guide wire extendable through a second of said channels to straighten said body during insertion of said sheath in the passageway of the patient and removable from said body after insertion so that said body resumes its normal predetermined shape in the passageway;
    a third channel for insertion of additional instruments; and
    a lock coupler attached to said proximate end of said body for attachment to a fitting to properly align and connect said sheath and its catheter and the additional instruments with external instrumentation.

2. Apparatus, as claimed in claim 1, wherein said lock coupler includes:
    a central opening for receiving the catheter; and
    a side opening for receiving the guide wire.

3. Apparatus, as claimed in claim 1, wherein:
    said guide wire comprises:
    a long, slender, substantially rigid body, having a distal end and a proximate end, receivable in said sheath body; and
    a handle attached to said proximate end of said guide wire body to aid in inserting and withdrawing said guide wire from said sheath.

4. A method of using an optical catheter in successive investigative and/or operative procedures, said method comprising the steps of:
    inserting a flexible optical catheter into an elongated sheath;
    inserting the sheath with the catheter in place therein into a passageway in the body of the patient;
    causing the sheath to assume a desired shape or orientation to properly position the catheter;
    conducting an investigative and/or operative procedure;
    removing the used sheath with the catheter in place therein from the passageway in the body of the patient;
    removing the catheter from the used sheath; and
    disposing of the used sheath.

5. A method, as claimed in claim 4, including the further steps of:
    inserting the catheter in a new sheath; and
    repeating the steps of claim 4.

6. A method of using an optical catheter in successive investigative and/or operative procedures, said method comprising the steps of:
    inserting a stiff wire into a flexible, elongated sheath, which has a predetermined curved shape which conforms to a specific passageway in the body of a patient, to straighten the sheath;
    inserting a flexible optical catheter into the sheath along side of the wire;
    inserting the sheath with the wire and catheter in place therein into a passageway in the body of a patient having the same shape as the predetermined curve of the sheath;
    removing the wire from the sheath so that the sheath and the catheter therein return to the predetermined shape of the sheath which now conforms with the shape of the passageway;
    conducting an investigative and/or operative procedure;
    removing the used sheath with the catheter in place therein from the passageway in the body of the patient;
    removing the catheter from the used sheath; and
    disposing of the used sheath.

7. A method, as claimed in claim 6, including the further steps of:
    inserting the catheter in a new sheath; and
    repeating the steps of claim 6.

* * * * *